United States Patent [19]

Cerri et al.

[11] Patent Number: 5,444,055
[45] Date of Patent: Aug. 22, 1995

[54] 17-HYDROXYIMINOMETHYL-5-β, 14 β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

[75] Inventors: Alberto Cerri, Gessate MI; Luigi Bernardi; Giuseppe Bianchi, both of Milan MI; Monica Florio, Bresso MI; Elena Folpini, Milan MI; Piero Melloni, Bresso MI, all of Italy

[73] Assignee: Sigma-Tau Industrie Farmaceutiche Riunite S.p.A., Rome, Italy

[21] Appl. No.: 106,892

[22] Filed: Aug. 16, 1993

[30] Foreign Application Priority Data

Aug. 20, 1992 [DE] Germany .................. 42 27 605.5

[51] Int. Cl.⁶ .................. C07J 41/00; C07J 1/00; A61K 31/565; A61K 31/57
[52] U.S. Cl. .................. 514/182; 552/582; 552/563; 552/520; 552/518; 552/610; 540/108; 514/176
[58] Field of Search ............. 552/582, 563, 520, 518, 552/610; 514/182

[56] References Cited

U.S. PATENT DOCUMENTS 3,019,242  1/1962  Wechter .................. 552/520

OTHER PUBLICATIONS

Templeton et al, J. Chem. Soc Perkins Trans. 1, Oct. 7, 1992, pp. 2503–2517.

Primary Examiner—Johann Richter
Assistant Examiner—Rebecca Cook
Attorney, Agent, or Firm—Oblon, Spivak, McClelland, Maier & Neustadt

[57] ABSTRACT

17-hydroxyiminomethyl-14β-hydroxy-5β androstane derivatives, active on the cardiovascular system, a process for their preparation and pharmaceutical compositions thereof having the general formula

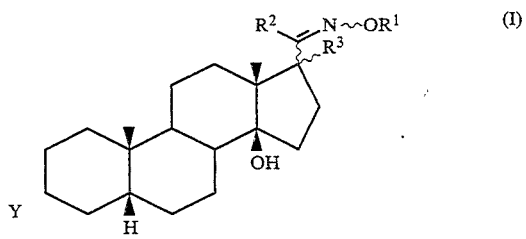

5 Claims, No Drawings

17-HYDROXYIMINOMETHYL-5-β, 14 β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

The present invention relates to new 17-hydroxyiminomethyl-14β-hydroxy-5β-androstane derivatives active on the cardiovascular system, to a process for their preparation and to pharmaceutical compositions containing same for the treatment of cardiovascular disorders, such as heart failure and hypertension. The compounds of the present invention have general formula (I):

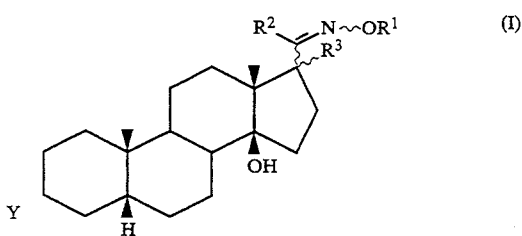

wherein:
the symbol ≡≡≡ represents a single or a double bond;
the symbol ⁓ means α or β configuration or a Z or E configuration;
when ≡≡≡ is a single bond, Y represents β-$OR^4$:
when ≡≡≡ is a double bond, Y represents a N⁓$OR^1$ or a N⁓NHC(=N⁓$R^5$)$NR^6R^7$ group;
$R^1$ represents hydrogen; methyl; C2–C6 alkyl, unsubstituted or substituted by one or more $NR^8R^9$ or NHC(=NH)$NH_2$;
$R^2$ represents hydrogen or methyl;
$R^3$ represents hydrogen or hydroxy;
$R^4$ represents hydrogen, C2–C4 alkyl unsubstituted or substituted by one or more $NR^{10}R^{11}$ or NHC(=NH)$NH_2$;
$R^5$ represents hydrogen, methyl or C2–C4 alkyl;
$R^6$, $R^7$ which may be the same or different, represent hydrogen, methyl or C2–C4 alkyl or $R^6$ and $R^7$ may form, taken together with the nitrogen atom, a five- or six-membered monoheterocyclic ring optionally containing other heteroatoms selected from oxygen and nitrogen;
$R^8$, $R^9$ which may be the same or different, represent hydrogen, methyl or C2–C4 alkyl or $R^8$ and $R^9$ may form, taken together with the nitrogen atom, a five- or six-membered monoheterocyclic ring optionally containing other heteroatoms selected from oxygen and nitrogen;
$R^{10}$, $R^{11}$ which may be the same or different, represent hydrogen, methyl or C2–C4 alkyl or $R^{10}$ and $R^{11}$ may form, taken together with the nitrogen atom, a five- or six-membered monoheterocyclic ring optionally containing other heteroatoms selected from oxygen and nitrogen;
$R^5$ and $R^6$ may form, together with the heteroatoms they are linked to and where possible, a five- or six- or seven-membered heteromonocyclic ring.

Where the compounds of formula (I) can exhibit tautomerism, the formula is intended to cover all tautomers; the invention includes within its scope all the possible stereoisomers, Z and E isomers, optical isomers and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e.g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

N-oxides of tertiary nitrogen atoms are also included in the invention.

The alkyl groups are branched or straight chain groups or cyclic groups.

The C2–C4 alkyl is preferably ethyl, n-propyl, iso-propyl, n-butyl or tert-butyl.

The C2–C6 alkyl is preferably ethyl, n-propyl, iso-propyl, n-butyl, tert-butyl or cyclohexyl.

The four-, five-, six- or seven-membered monoheterocyclic ring is preferably 3-pyrrolidinyl, 3-piperidyl, 4-piperidyl, 2,3,4,5,6,7-hexahydro-1H-azepin-3-yl, 2,3,4,5,6,7-hexahydro-1H-azepin-4-yl.

The $R^1$ group is preferably hydrogen, methyl, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl, 3-guanidinopropyl.

The $R^4$ group is preferably hydrogen, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl, 3-guanidinopropyl.

The $R^5$ group is preferably hydrogen, methyl, ethyl or iso-propyl.

The $NR^6R^7$ group is preferably amino, methylamino, dimethylamino, diethylamino, iso-propylamino, pyrrolidinyl, piperidyl, morfolino, piperazin-1-yl, 4-methylpiperazin-1-yl, morpholino.

The $NR^8R^9$ group is preferably amino, methylamino, dimethylamino, diethylamino, iso-propylamino, pyrrolidinyl, piperidyl, morfolino, piperazin-1-yl, 4-methylpiperazin-1-yl, morpholino.

The $NR^{10}R^{11}$ group is preferably amino, methylamino, dimethylamino, ethylamino, diethylamino, iso-propylamino, pyrrolidinyl, morfolino.

When $R^5$ and $R^6$, taken together with the heteroatoms they are linked to, form a heterocyclic ring this is preferably 2-(2-imidazolinyl), 1-methyl-2-imidazolin-2-yl, 1,4,5,6-tetrahydro-2-pyrimidinyl, 1-methyl-1,4,5,6-tetrahydro-2-pyrimidinyl. Preferred examples of specific compounds according to the present invention are (E)- 17β-hydroxyiminomethyl-5β-androstane-3β,14β-diol (E)- 17β-methoxyiminomethyl-5β-androstane-3β,14β-diol (E)- 17β-(2-aminoethoxyimino)methyl-5β-androstane-3β,14β-diol (E)- 17β-(3-aminopropoxyimino)methyl-5β-androstane-3β,14β-diol (E)- 17β-(2-dimethylaminoethoxyimino)methyl-5β-androstane-3β,14β-diol (E)-17β-(3-dimethylaminopropoxyimino)methyl-5β-androstane-3β,14β-diol (E)-17β-(2-guanidinoethoxyimino)methyl-5β-androstane-3β,14β-diol (E)-17β-(3-guanidinopropoxyimino)methyl-5β-androstane-3β,14β-diol (E -20-hydroxyimino-5β-pregnane-3β,14β-diol (E)-20-(2-aminoethoxyimino)-5β-pregnane-3β,14β-diol (E)-20-(2-dimethylaminoethoxyimino)-5β-pregnane-3β,14β-diol (E)-20-(3-aminopropoxyimino)-5β-pregnane-3β,14β-diol (E)-20-(3-dimethylaminopropoxyimino)-5β-pregnane-3β,14β-diol (E)-17β-hydroxyiminomethyl-5β-androstane-3β,14β,17α-triol (E)-17β-methoxyiminomethyl-5β-androstane-3β,14β,17α-triol (E)-17β-(2-aminoethoxyimino)methyl-5β-androstane-3β,14β,17α-triol (E)-17β-(3-aminopropoxyimino)methyl-5β-androstane-3β,14β,17α-triol (E)-17β-(2-dimethylaminoethoxyimino)methyl-5β-androstane-3β,14β,17α-triol (E)-17β-(3-dimethylaminopropoxyimino)methyl-5β-androstane-3β,14β,17α-triol (E)-17β-(2-guanidinoethoxyimino)methyl-5β-androstane-3b,14b,17α-triol (E)-17β-(3-guanidinopropoxyimino)methyl-5β-androstane-3β,14β,17α-triol (E)-20-(2-aminoethoxyimino)-5β-pregnane-3β,14β,17β-triol (E)-20-(2-dimethylaminoethoxyimino)-5β-pregnane-3β,14β,17α-triol (E)-20-(3-aminopropoxyimino)-5β-pregnane-3β,14β,17α-triol (E)-20-(3-dimethylaminopropoxyimino)-5β-pregnane-3β,14β,17α-triol (E)-3β-(3-aminopropoxy)-17β-hydroxyiminomethyl-5β-androstane-14β-ol (E)-3β-(3-aminopropoxy)-17β-methoxyiminomethyl-5β-androstane-14β-ol (E)-3β-(3-aminopropoxy)-17β-(2-aminoethoxyimino)methyl-5β-androstane-14β-ol (E)-3β-(3-aminopropoxy)-17β-(3-aminopropoxyimino)methyl-5β-androstane-14β-ol (E)-3β-(3-aminopropoxy)-17β-(2-dimethylaminoethoxyimino)methyl-5β-androstane-14β-ol (E)-3β-(3-aminopropoxy)-17β-(3-dimethylaminopropoxyimino)methyl-5β-androstane-14β-ol (E)-3β-(3-aminopropoxy)-17β-(2-guanidinoethoxyimino)methyl-5β-androstane-14β-ol (E)-3β-(3-aminopropoxy)-17β-(3-guanidinopropoxyimino)methyl-5β-androstane-14β-ol (E)-3β-(3-aminopropoxy)-20-(2-aminoethoxyimino)-5β-pregnane-14β-ol (E)-3β-(3-aminopropoxy)-20-(2-dimethylaminoethoxyimino)-5β-pregnane-14β-ol (E)-3β-(3-aminopropoxy)-20-(3-aminopropoxyimino)-5β-pregnane-14β-ol (E)-3β-(3-aminopropoxy)-20-(3-dimethylaminopropoxyimino)-5β-pregnane-14β-ol (E)-3β-(3-aminopropoxy)-17β-hydroxyiminomethyl-5β-androstane-14β,17α-diol (E)-3β-(3-aminopropoxy)-17β-methoxyiminomethyl-5β-androstane-14β,17α-diol (E)-3β-(3-aminopropoxy)-17β-(2-aminoethoxyimino)methyl-5β-androstane-14β,17α-diol (E)-3β-(3-aminopropoxy)-17β-(3-aminopropoxyimino)methyl-5β-androstane-14β,17α-diol (E)-3β-(3-aminopropoxy)-17β-(2-dimethylaminoethoxyimino)methyl-5β-androstane-14β,17α-diol (E)-3β-(3-aminopropoxy)-17β-(3-dimethylaminopropoxyimino)methyl-5β-androstane-14β,17α-diol (E)-3β-(3-aminopropoxy)-17β-(2-guanidinoethoxyimino)methyl-5β-androstane-14β,17α-diol (E)-3β-(3-aminopropoxy)-17β-(3-guanidinopropoxyimino)methyl-5β-androstane-14β,17α-diol 3-((EZ)-guanidinoimino)-17β-((E)-2-aminoethoxyiminomethyl)-5β-androstane-14β-ol 3-((EZ)-guanidinoimino)-17β-((E)-3-aminopropoxyiminomethyl)-5β-androstane-14β-ol 3-((EZ)-guanidinoimino)-17β-((E)-2-dimethylaminoethoxyiminomethyl)-5β-androstane-14β-ol 3-((EZ)-guanidinoimino)-17β-((E)-3-dimethylaminopropoxyiminomethyl)-5β-androstane-14β-ol 3-((EZ)-(2-imidazolin-2-yl)idrazono)-17β-((E)-2-dimethylaminoethoxyiminomethyl)-5β-androstane-14β-ol 3-((EZ)-(2-imidazolin-2-yl)idrazono)-17β-((E)-3-dimethylaminopropoxyiminomethyl)-5β-androstane-14β-ol 3-((EZ)-(2-dimethylaminoethoxyimino)-17β-((E)-2-dimethylaminoethoxyiminomethyl)-5β-androstane-14β-ol 3-((EZ)-3-dimethylaminopropoxyimino)-17β-((E)-3-dimethylaminopropoxyiminomethyl)-5β-androstane-14β-ol and where there are the (E) isomers also the corresponding (Z) isomers;

and where there are the 3β-(3-aminopropoxy) substituents also the corresponding 3β-(3-dimethylaminopropoxy), 3β-(3-diethylaminopropoxy), 3β-(3-(1-pyrrolidinyl)propoxy), 3β-(2-aminoethoxy), 3β-(2-dimethylaminoethoxy), 3β-(2-diethylaminoethoxy) and 3β-(2-(1-pyrrolidinyl)ethoxy) are preferred compounds.

Some 17β-iminomethyl-5β-androstane-3β,14β-diol derivatives are reported to be weak inhibitors of Na+,K+-ATPase and weak positive inotropic agents (17β-guanidinoiminomethyl-5β-androstane-3β,14β-diol (Gelbart A. and Thomas R., *J. Med. Chem.*, 5 1978, 21, 284) and 17-guanidinoimino-5β-androstane-3β,14β-diol (Schönfeld W. and Repke K., Quant. Struct.-Act. Relat., 1988, 7, 160)); other 20-substituted iminomethyl-5β-androstane-3β,14β-diols (20-ureidoimino, 20-idrazono) are reported not to inhibit Na+,K+-ATPase (Thomas R. et al., *J. Pharmacol. Exp. Ther.*, 1974, 191 ,219; Boutagy J. et al., *Aust. J. Pharm. Sci.*, 1973, 2, 41).

Particularly two 17β-hydroxyiminomethyl-5β-androstane-3β,14β-diol derivatives are known: 17β-hydroxyiminomethyl-5β-androstane-3b,14b-diol is reported not to inhibit Na+,K+-ATPase (Thomas R. et al., *Adv. Drug Res.*, 1990, 19, 311) and 3β-acetoxy-20-methoxyimino-5β-pregnane-14β,21-diol is reported as intermediate for 14β,21-epoxypregnan-20-ones claimed in U.S. Pat. No. 3,146,230.

The invention furthermore provides a process for the preparation of compounds of general formula (I), which comprises the condensation reaction of compounds of formula (II)

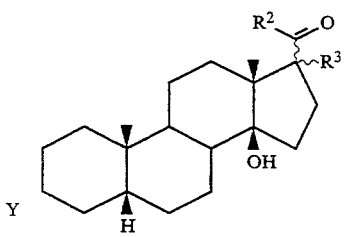 (II)

in which: Y,═, R² and R³ are as above defined, with compounds of general formula (III)

 (III)

to give compounds of general formula (I) where R¹ is as above defined. Compounds (III) can be used as the free base or in the form of a salt with an acid such as, e.g., hydrochloric, carbonic, oxalic, hydriodic or sulfuric acid. The reaction can be carried out in a solvent, such as ethanol, methanol, acetonitrile, dioxane, tetrahydrofuran, water or a mixture of said solvents, at a temperature between 0° C. and the boiling point of the above mentioned solvents or of their mixtures. To the reaction mixtures, additional salts, such as, e.g., $NaH_2PO_4$, $Na_2HPO_4$, NaOAc, can be added as well as acids such as, e.g., hydrochloric, sulfuric, acetic, phosphoric acid, and bases such as, e.g., sodium or potassium hydroxide, to maintain the desired pH.

The groups optionally present in Y and/or R² and/or R³ are protected, if necessary, by known methods, to give after removal of protective groups, if any, compounds of general formula (I) which can be converted into other compounds of general formula (I) by known methods.

Compounds of formula (I) where Y is β-OR⁴ where R¹ and/or R⁴ contain a guanidino group can be obtained by reacting a compound of formula (I) where Y is β-OR⁴ where R¹ and/or R⁴ contain a primary mine with e.g. 1-amidino-3,5-dimethylpyrazole nitrate.

Said transformation is only an example of well established procedures described in Organic Chemistry (see for example: J. March "Advanced Organic Chemistry", J. Wiley & Sons, 1985; D. Barton and W. D. Ollis "Comprehensive Organic Chemistry", Pergamon Press, 1979) well known to those skilled in the art.

Compounds of general formula (II) where Y is oxygen when ═ is a double bond, or 3β-hydroxy when ─ is a single bond, wherein R² and R³ are as above defined are known compounds (Boutagy J. and Thomas R., Aust. J. Chem., 1971, 24, 2723; Boutagy J. and Thomas R., Aust. J. Pharm. Sci., (NS), 1973, 2, 9; Templeton J. F. et al., J. Med. Chem., 1989, 32, 1977; Templeton J. F. et al., J. Chem. Soc., Perkin Trans. 1, 1991, 823; Danieli N. et al., Tetrahedron, 1967, 23, 715) or are prepared from known compounds with methods well known to those skilled in the art.

For example the unknown 3β-hydroxy compounds are prepared from the corresponding known 3-keto compounds by reduction with Li-selectride.

Conversely, when the 3β-hydroxy is a known compound the corresponding unknown 3-keto compound is obtained by oxidation with known oxidants such as Jones reagent, chromic anhydride in pyridine or tetrapropylammonium perruthenate and N-methylmorpholine-N-oxide.

When the 17α-hydroxy-20-carbonyl compounds are unknown compounds they are obtained from the corresponding 17α-hydrogen-20-carbonyl compounds by careful oxidation with selenium dioxide in a solvent such as, e.g., dioxane, in the presence of a base such as, e.g., pyridine or triethylamine, at a temperature ranging from 20° C. to the boiling point of the solvent.

Unknown 17α-formylandrostanes and 20-oxo-17α-pregnanes derivatives are prepared from the corresponding 20-oxo-17β-epimeric compounds, unsubstituted in position 17α, by isomerization in alkaline conditions. The introduction of the hydroxy group in position 17β is performed with the methods described above for the corresponding 17β epimers.

Compounds (II) where ═ is a double bond and Y is a N~OR¹ or a N~NHC(═N~R⁵)NR⁶R⁷ group are obtained from compounds (II) where Y is oxygen and ~ is a double bond by reaction with a compound of formula (III) or (IV).

 (IV)

Compounds (II) where ─ is a single bond and Y is OR⁴, where R⁴ is different from hydrogen, are prepared from the corresponding compounds (II) where Y is 3β-hydroxy, by reaction with a compound of formula (V)

 (V)

where R4 is different from hydrogen and W is an electron-withdrawing group, such as halogen, mesyloxy, or tosyloxy group, which confers electrophilic properties to the attached carbon atom, and R⁴ is as above defined. The reaction is best carried out in an inert aprotic solvent, such as tetrahydrofuran, dioxane, dimethylformamide, dimethylsulfoxyde or in neat R⁴W and in the presence of a base such as, e.g., sodium or potassium hydride, at a temperature ranging from 0° C. to 110° C.

The groups optionally present in Y and/or R² and/or R³ are protected, if necessary, by known methods, to give, after removal by known methods of protective groups, if any, possibly present in Y and/or R² and/or R³, a compound of general formula (II).

Compounds of general formula (III), (IV) and (V) are known compounds, generally commercially available or preparable from known compounds by known methods.

Compounds of general formula (I) prepared according to the invention and their pharmaceutically acceptable salts are useful agents for the treatment of cardiovascular disorders such as heart failure and hypertension.

The compounds of general formula (I) prepared according to the invention and their pharmaceutically acceptable salts have highly reduced toxicity compared to known positive inotropic agents such as ouabain and digitoxin.

Moreover said compounds (I) show good affinity for the receptor site of the $Na^+,K^+$-ATPase and behave as partial agonists on the enzimatic activity of the $Na^+,K^+$-ATPase.

To test the affinity for the receptor site of the $Na^+,K^+$-ATPase and the agonist or antagonist activity on the enzyme, the following tests were used:

a) displacement of the specific ³H-ouabain binding from the $Na^+,K^+$-ATPase receptor purified according to Jorghensen (Jorghensen P., BBA, 1974, 356, 36) and Erdmann (Erdmann E. et al., Arzneim. Forsh., 1984, 34, 1314);

b) inhibition of the activity of the purified Na+,K+-ATPase measured as % of hydrolysis of $^{32}$P-ATP in presence and in absence of the tested compound (Mall F. et al., Biochem. Pharmacol., 1984, 33, 47)

Systolic blood pressure (SBP) and heart rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5% (w/v), was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment mantained blood pressure low or reestablished the basal values.

The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., Japan J. Pharmacol., 1979, 29, 171; Takeda K. et al. Japan J. Pharmacol., 1982, 32, 283; Richer C. et al. Eur. J. Pharmacol, 1978, 47,393).

The affinity and the inhibitory activity of some compounds in the two tests are shown in the following table:

| | Binding $^3$H-Ouab. Displacement −log IC50 | Inhibitory Activity −log IC50 |
|---|---|---|
| Comp. I-aa | 5.4 | 4.5 |
| Comp. I-ab | 7.1 | 5.8 |
| Comp. I-ad | 7.4 | 5.9 |
| Comp. I-af | 6.8 | 5.6 |
| Comp. I-ag | 6.8 | 5.5 |
| Comp. I-ai | 7.1 | 5.7 |
| Comp. I-ak | 6.0 | 4.4 |
| Comp. I-am | 6.0 | 4.6 |
| Comp. I-an | 5.8 | 4.6 |
| Comp. I-ao | 5.9 | 4.6 |
| Comp. I-ap | 5.7 | 4.5 |
| Comp. I-aq | 6.2 | 4.8 |
| Comp. I-ar | 6.1 | 4.8 |
| Comp. I-as | 7.4 | 6.5 |
| Comp. I-au | 7.3 | 6.4 |
| Comp. I-aw | 7.1 | 5.9 |
| Comp. I-az | 6.9 | 5.7 |

The activity of some new compound in preventing the development of hypertension is shown in the following table:

EFFECT OF 5 WEEK-TREATMENT IN SPONTANEOUS HYPERTENSIVE RATS (MHS) ON THE DEVELOPMENT OF HYPERTENSION

| Compound | RATS | DOSE* mg/Kg/os | SBP mm Hg | HR beats/min. |
|---|---|---|---|---|
| Controls | 7 | Methocel | 173 +/− 4.5 | 382 +/− 8.3 |
| Comp. I-ad | 7 | 20 | 148 +/− 4.0 | 375 +/− 10.5 |
| Comp. I-ar | 7 | 20 | 158 +/− 4.0 | 385 +/− 6.4 |
| Comp. I-as | 7 | 20 | 149 +/− 7.9 | 377 +/− 9.5 |

*in Methocel 0.5% w/v

The following examples illustrate the invention without limiting it.

EXAMPLE 1

(E)-17β-Methoxyiminomethyl-5β-androstane-3β,14β-diol (I-aa)

To a suspension of 0.16 g of methoxylamine hydrochloride and 0.19 g of NaHCO₃ in 12 ml of dioxane and 10 ml of water a solution of 0.50 g of 3β,14β-dihydroxy-5β-androstane-17β-carboxaldehyde (Boutagy J. and Thomas R., Aust. J. Chem., 1971, 24, 2723) in 6 ml of dioxane was added dropwise at room temperature. After 15 minutes the solution was diluted with water and extracted with chloroform; the organic layer was dried over anhydrous sodium sulfate and evaporated to dryness. The crude product was purified by flash-chromatography (SiO₂) using cyclohexane/ethyl acetate 60/40; the fractions containing the rifle compound were collected and evaporated to dryness. The residue was ground with di-iso-propyl ether/ethanol to give 0.20 g of the title compound (I-aa), as a white solid.

$^1$H-NMR (300 MHz, CDCl₃, ppm from TMS): 0.93 (3H, s); 0.98 (3H, s); 2.35–2.45 (1H, m); 3.80 (3H, s); 4.12 (1H, m); 7.55 (1H, d).

EXAMPLE 2

(E)-17β-(2-Aminoethoxyimino)methyl-5β-androstane-3β-diol (I-ab)

To a suspension of 6.30 g of NaH₂PO₄.H₂O, 3.50 g of Na₂HPO₄.12H2O and 0.65 g of 2-aminoethoxyamine dihydrochloride in 20 ml of dioxane and 40 ml of water a solution of 1.00 g of 3β,14β-dihydroxy-5β-androstane-17β-carboxaldehyde (Boutagy J. and Thomas R., Aust. J. Chem., 1971, 24, 2723) in 50 ml of dioxane was added dropwise at room temperature. After 18 hrs the solution was alkalinized with an acqueous solution of NaHCO₃ and extracted with ethyl acetate; the organic layer was dried over anhydrous sodium sulfate and evaporated to dryness. The crude product was dissolved in ethyl acetate and 0.20 g of oxalic acid were added. The precipitate was collected by filtration and ground with ethyl acetate/ethanol to give 0.34 g of the title compound (I-ab) as an oxalate, white solid.

$^1$H-NMR (300 MHz, CD₃OD, ppm from TMS): 0.78 (3H, s); 0.88 (3H, s); 2.23 (1H, m); 3.20 (2H, m); 3.88 (1H, m); 4.18 (2H, m); 7.55 (1H, d).

EXAMPLE 3

(E)-17β-(3-Aminopropoxyimino)methyl-5β-androstane-3β,14β-diol (I-ac)

The title compound (I-ac) (0.23 g) was obtained as an oxalate salt, starting from 3β,14β-dihydroxy-5β-androstane-17β-carboxaldehyde (0.50 g) (Boutagy J. and Thomas R., Aust. J. Chem., 1971, 24, 2723) and 3-aminopropoxyamine dihydrochloride using the procedure described in Ex. 2.

$^1$H-NMR (300 MHz, DMSO-d$_6$, ppm from TMS): 0.77 (3H, s); 0.86 (3H, s); 2.23 (1H, m); 3.12 (2H, m); 3.86 (1H, m); 4.10 (2H, m); 7.56 (1H, d).

EXAMPLE 4

(E)-17β-(2-Dimethylaminoethoxyimino)methyl-5β-androstane-3β,14 β-diol (I-ad)

The title compound (I-ad) (0.28 g) was obtained as an oxalate salt, starting from 3β,14β-dihydroxy-5β-androstane-17β-carboxaldehyde (0.60 g) (Boutagy J. and Thomas R., *Aust. J. Chem.*, 1971, 24, 2723) and 2-dimethylaminoethoxyamine dihydrochloride using the procedure described in Ex. 2.

$^1$H-NMR (300 MHz, DMSO-d$_6$, ppm from TMS): 0.77 (3H, s); 0.86 (3H, s); 2.22 (1H, m); 2.71 (6H, s); 3.22 (2H, m); 3.87 (1H, m); 4.18 (2H, m); 7.54 (1H, d).

EXAMPLE 5

(Z)-17β-(2-Dimethylaminoethoxyimino)methyl-5β-androstane-3β,14β-diol (I-ae)

The title compound (I-ae) (0.10 g) was isolated from the (E) isomer of Ex. 4 by flash chromatography of the mother liquors of the salification, using chloroform/methanol/28% ammonium hydroxide 89/10/1 as eluant.

$^1$H-NMR (300 MHz, CD$_3$OD, ppm from TMS): 0.90 (3H, s); 0.97 (3H; m); 2.88 (1H, m); 4.05 (1H, m); 6.98 (1H, d).

EXAMPLE 6

(E)-17β-(3-Dimethylaminopropoxyimino)methyl-5.β-androstane-3β,14β-diol (I-af)

The title compound (I-af) (0.23 g) was obtained as an oxalate salt, starting from 3β,14β-dihydroxy-5β-androstane-17β-carboxaldehyde (0.50 g) (Boutagy J. and Thomas R., *Aust. J. Chem.*, 1971, 24, 2723) and 3-dimethylaminopropoxyamine dihydrochloride using the procedure described in Ex. 2.

$^1$H-NMR (300 MHz, DMSO-d$_6$, ppm from TMS): 0.75 (3H, s); 0.85 (3H, s); 2.23 (1H, m); 2.65 (6H, s); 3.10 (2H, m); 3.87 (1H, m); 4.10 (2H, m); 7.52 (1H, d).

EXAMPLE 7

(E)-17β-(2-Guanidinoethoxyimino)methyl-5β-androstane-3β,14β-diol (I-ag)

A solution of 0.95 g of (E)-17β-(2-aminoethoxyimino)methyl-5β-androstane-3β,14β-diol (I-ab) and 1.05 g of 1-amidino-3,5-dimethylpyrazole nitrate in 20 ml of ethanol was heated at reflux for 10 hrs. The solution was evaporated to dryness under reduced pressure and the crude product was purified by flash-chromatography (SiO$_2$) using chloroform/methanol/28% ammonium hydroxide 78/20/2 as eluant; the fractions containing the title compound were collected and evaporated to dryness under reduced pressure. The residue was ground with di-iso-propyl ether/ethanol to give 0.38 g of the title compound (I-ag), as a nitrate, white solid.

$^1$H-NMR (300 MHz, DMSO-d$_6$, ppm from TMS): 0.77 (3H, s); 0.86 (3H, s); 2.22 (1H, m); 3.32 (2H, m); 3.88 (1H, m); 4.15 (2H, m); 7.52 (1H, d).

EXAMPLE 8

(E)-17β-(3-Guanidinopropoxyimino)methyl-5β-androstane-3β,14β-diol (I-ah)

The title compound (I-ah) (0.23 g) was obtained as a nitrate salt, starting from (E)-17β-(3-aminopropoxyimino)methyl-5β-androstane-3β,14β-diol (0.65 g) (I-ac) and 1-amidino-3,5-dimethylpyrazole nitrate using the procedure described in Ex. 7.

$^1$H-NMR (300 MHz, DMSO-d$_6$, ppm from TMS): 0.75 (3H, s); 0.85 (3H, s); 2.22 (1H, m); 3.20 (2H, m); 3.87 (1H, m); 4.11 (2H, m); 7.51 (1H, d).

EXAMPLE 9

(E)-20-(2-Dimethylaminoethoxyimino)-5β-pregnane-3β,14β-diol (I-ai)

The title compound (I-ai) (0.27 g) was obtained as an oxalate salt, starting from 3β,14β-dihydroxy-5β-pregnan-20-one (0.68 g) (Templeton J. F. et al., *J. Chem. Soc., Perkin Trans.* 1, 1991, 823) and 2-dimethylaminoethoxyamine dihydrochloride using the procedure described in Ex. 2.

$^1$H-NMR (300 MHz, DMSO-d$_6$, ppm from TMS): 0.75 (3H, s); 0.86 (3H, s); 1.95 (3H, s); 2.70 (6H, s); 3.21 (2H, m); 3.86 (1H, m); 4.16 (2H, m).

EXAMPLE 10

(E)-17β-Hydroxyiminomethyl-5β-androstane-3β,14β,17α-triol (I-aj)

To a solution of 0.08 g of hydroxylamine hydrochloride in 7.5 ml of 0.1M sodium hydroxide a solution of 0.24 g of 3β-acetoxy-14β,17α-dihydroxy-5β-androstane-17β-carboxaldehyde (Prepn. 1) in 20 ml of dioxane was added dropwise. After 2 hrs at reflux temperature, 0.75 ml of 1M sodium hydroxide were added and the solution was refluxed for 4 hrs. The mixture was evaporated to dryness under reduced pressure. The crude product was ground with ethanol/water and then with ethanol/diethyl ether to give 0.18 g of the title compound (I-aj) as a white solid.

$^1$H-NMR (300 MHz, CDCl$_3$, ppm from TMS): 0.85 (3H, s); 0.95 (3H, s); 7.72 (1H, s).

EXAMPLE 11

(E)-17β-(2-Dimethylaminoethoxyimino)methyl-5β-androstane-3β,14β,17α-triol (I-ak)

The title compound (I-ak) (0.23 g) was obtained starting from 3β-acetoxy-14β,17α-dihydroxy-5β-androstane-17β-carboxaldehyde (0.65 g) (Prepn. 1) and 3-dimethylaminoethoxyamine dihydrochloride using the procedure described in Ex. 10.

$^1$H-NMR (300 MHz, CD$_3$OD, ppm from TMS): 0.87 (3H, s); 0.97 (3H, s); 2.35 (6H, s); 2.71 (2H, t); 4.05 (1H, m); 4.18 (2H, t); 7.90 (1H, s).

EXAMPLE 12

(E)-17β-(3-Dimethylaminopropoxyimino)methyl-5β-androstane-3β,14β,17α-triol (I-al)

The title compound (I-al) (0.29 g) was obtained starting from 3β-acetoxy-14β,17α-dihydroxy-5β-androstane-17β-carboxaldehyde (0.58 g) (Prepn. 1) and 3-dimethylaminopropoxyamine dihydrochloride using the procedure described in Ex. 10.

$^1$H-NMR (300 MHz, CD$_3$OD, ppm from TMS): 0.87 (3H, s); 0.97 (3H, s); 2.20 (6H, s); 2.60 (2H, t); 4.05 (1H, m); 4.10 (2H, t); 7.90 (1H, s).

EXAMPLE 13

(E)-3β-(3-Aminopropoxy)-17β-hydroxyiminomethyl-5β-androstane-14β-ol (I-am)

A solution of 1.00 g of 3β-(3-aminopropoxy)-17β-(2-(1,3-dioxolanyl))-5β-androstane-14β-ol (Prepn. 2) and 1.00 g of hydroxylamine hydrochloride in 30 ml of 0.01M hydrochloric acid and 80 ml of dioxane was kept at room temperature for 2 days and then evaporated to dryness under reduced pressure. The crude product was purified by flash-chromatography (SiO$_2$) using chloroform/methanol/28% ammonium hydroxide 89/10/1 as eluant. The fractions containing the title compound were collected and evaporated to dryness. The residue was ground with ethanol/ethyl ether to give 0.33 g of the title compound (I-am) as a white solid.

$^1$H-NMR (300 MHz, CDCl$_3$, ppm from TMS): 0.94 (6H, s); 2.40 (1H, m); 2.68 (2H, t); 3.43 (2H, m); 3.61 (1H, m); 7.61 (1H, d).

EXAMPLE 14

(E)-3β-(2-Aminoethoxy)-17β-hydroxyiminomethyl-5β-androstane-14β-ol (I-an)

The title compound (I-an) (0.40 g) was obtained as a white solid starting from 3β-(2-aminoethoxy)-17β-(2-(1,3-dioxolanyl))-5β-androstane-14β-ol (0.80 g) (Prepn. 3) and hydroxylamine hydrochloride using the same procedure described in Ex. 13.

$^1$H-NMR (300 MHz, CDCl$_3$, ppm from TMS): 0.95 (6H, s); 2.40 (1H, m); 2.85 (2H, t); 3.40 (2H, m); 3.65 (1H, m); 7.60 (1H, d).

EXAMPLE 15

(E)-3β-(2-(1-Pyrrrolidinyl)ethoxy)-17β-hyrdroxyiminomethyl-5β-androstane-14β-ol (I-ao)

The title compound (I-ao) (0.25 g) was obtained as a white solid starting from 3β-(2-(1-pyrrolidinyl)ethoxy)-17β-(2-(1,3-dioxolanyl))-5β-androstane-14β-ol (0.80 g) (Prepn. 4) and hydroxylamine hydrochloride using the same procedure described in Ex. 13.

$^1$H-NMR (300 MHz, CDCl$_3$, ppm from TMS): 0.93 (6H, s); 2.41 (1H, m); 2.59 (4H, m); 2.70 (2H, t); 3.52 (2H, m); 3.62 (1H, m); 7.62 (1H, d).

EXAMPLE 16

(E)-3β-(3-(1-Pyrrrolidinyl)propoxy)-17β-hydroxyiminomethyl-5β-androstane-14β-ol (I-ap)

The title compound (I-ap) (0.28 g) was obtained as a white solid starting from 3β-(3-( 1-pyrrolidinyl)propoxy)-17β-(2-(1,3-dioxolanyl))-5β-androstane-14β-ol (0.80 g) (Prepn. 5) and hydroxylamine hydrochloride using the same procedure described in Ex. 13.

$^1$H-NMR (300 MHz, CDCl$_3$, ppm from TMS): 0.93 (6H, s); 2.40 (1H, m); 2.55 (6H, m); 3.40 (2H, m); 3.60 (1H, m); 7.60 (1H, d).

EXAMPLE 17

(E)-3β-(3-Aminopropoxy)-17β-methoxyiminomethyl-5β-androstane-14β-ol (I-aq)

The title compound (I-aq) (0.42 g) was obtained as a white solid starting from 3β-(3-aminopropoxy)-17β-(2-(1,3-dioxolanyl))-5β-androstane-14β-ol (0.90 g) (Prepn. 2) and methoxylamine hydrochloride using the same procedure described in Ex. 13.

$^1$H-NMR (300 MHz, CDCl$_3$, ppm from TMS): 0.94 (6H, s); 2.40 (1H, m); 2.73 (2H, t); 3.45 (2H, m); 3.62 (1H, m); 3.80 (3H, s); 7.63 (1H, d).

EXAMPLE 18

(E)-3β(2-(1-Pyrrolidinyl)ethoxy)-17β-methoxyimino)-methyl-5β-androstane-14β-ol (I-ar)

The title compound (I-ar) (0.42 g) was obtained as a white solid starting from 3β-(2-(1-pyrrolidinyl)ethoxy)-17β-(2-(1,3dioxolanyl))-5β-androstane-14β-ol (0.90 g) (Prepn. 4) and methoxylamine hydrochloride using the same procedure described in Ex. 13.

$^1$H-NMR (300 MHz, CDCl$_3$, ppm from TMS): 0.93 (6H, s); 2.41 (1H, m); 2.59 (4H, m); 2.70 (2H, t); 3.52 (2H, m); 3.62 (1H, m); 3.81 (3H, s); 7.62 (1H, d).

EXAMPLE 19

(E)-3β-(3-Aminopropoxy)-17β-(2-dimethylaminoethoxyimino)methyl-5β-androstane-14β-ol (I-as)

The title compound (I-as) (0.19 g) was obtained as a white solid starting from 3β-(3-aminopropoxy)-17β-(2-(1,3-dioxolanyl))-5β-androstane-14β-ol (1.00 g)(Prepn. 2) and 2-dimethylaminoethoxyamine dihydrochloride using the same procedure described in Ex. 13.

$^1$H-NMR (300 MHz, DMSO-d$_6$, ppm from TMS): 0.76 (3H, s); 0.87 (3H, s); 2.25 (1H, m); 2.57 (2H, t); 2.70 (6H, s); 3.22 (2H, t); 3.35 (2H, m); 3.54 (1H, m); 3.90 (1H, s); 4.19 (2H, t); 7.52 (1H, d).

EXAMPLE 20

(E)-3β-(2-Aminoethoxy)-17β-(2-dimethylaminoethoxyimino)-methyl-5β-androstane-14β-ol (I-at)

The title compound (I-at) (0.21 g) was obtained as a white solid starting from 3β-(2-aminoethoxy)-17β-(2-(1,3-dioxolanyl))-5β-androstane-14β-ol (0.80 g) (Prepn. 3) and 2-dimethylaminoethoxyamine dihydrochloride using the same procedure described in Ex. 13.

$^1$H-NMR (300 MHz, DMSO-d$_6$, ppm from TMS): 0.75 (3H, s); 0.87 (3H, s); 2.25 (1H, m); 2.60 (2H, t); 2.70 (6H, s); 3.20 (2H, t); 3.40 (2H, m); 3.60 (1H, m); 3.90 (1H, s); 4.20 (2H, t); 7.52 (1H, d).

EXAMPLE 21

(E)-3β-(2-(1-Pyrrolidinyl)ethoxy)-17β-(2-dimethylaminoethoxyimino)methyl-5β-androstane-3β,14β-diol (I-au)

The title compound (I-au) (0.19 g) was obtained as a white solid starting from 3β-(2-(1-pyrrolidinyl)ethoxy)-17β-(2-(1,3-dioxolanyl))-5β-androstane-14β-ol (1.00 g) (Prepn. 4) and 2-dimethylaminoethoxyamine dihydrochloride using the same procedure described in Ex. 13.

$^1$H-NMR (300 MHz, DMSO-d$_6$, ppm from TMS): 0.76 (3H, s); 0.86 (3H, s); 2.25 (1H, m); 2.47 (4H, m); 2.53 (2H, t); 2.71 (6H, s); 3.22 (2H, t); 3.38 (2H, m); 3.55 (1H, m); 3.90 (1H, s); 4.18 (2H, t); 7.53 (1H, d).

EXAMPLE 22

(E)-3β-(3-(1-Pyrrolidinyl)propoxy)-17β-(2-dimethylaminoethoxyimino)methyl-5β-androstane-3β,14β-diol (I-av)

The title compound (I-av) (0.23 g) was obtained as a white foam starting from 3β-(3-( 1-pyrrolidinyl)propoxy)-17β-(2-( 1,3-dioxolanyl))-5β-androstane-14β-ol (0.80 g) (Prepn. 5) and 2dimethylaminoethoxyamine dihydrochloride using the same procedure described in Ex. 13.

$^1$H-NMR (300 MHz, DMSO-d$_6$, ppm from TMS): 0.76 (3H, s); 0.86 (3H, s); 2.25 (1H, m); 2.45 (6H, m); 2.70 (6H, s); 3.22 (2H, t); 3.30 (2H, m); 3.55 (1H, m); 3.90 (1H, s); 4.20 (2H, t); 7.55 (1H, d).

EXAMPLE 23

3-((EZ)-Guanidinoimino)-17β-((E)-2-dimethylaminoethoxyiminomethyl)-5β-androstane-14β-ol (I-aw)

To a solution of 0.21 g of 2-dimethylaminoethoxyamine dihydrochloride, 2.00 g of sodium acetate in 25 ml of 0.2M acetic acid a solution of 0.30 g of 3-oxo-14β-hydroxy-5β-androstane-17β-carboxaldehyde (Prepn. 6) in 40 ml of dioxane was added dropwise. After 2 hrs at room temperature, the mixture was evaporated to dryness under reduced pressure and the crude product was extracted three times with iso-propanol. Evaporation of the solvent gave 0.33 g of (E)-3-oxo-17β-(2-dimethylaminoethoxyiminomethyl)-5β-androstane-14β-ol acetate as a white foam.

$^1$H-NMR (300 MHz, DMSO-d$_6$, ppm from TMS):
0.79 (3H, s); 0.88 (3H, s); 1.85 (3H, s); 2.25 (1H, m); 2.70 (1H, m); 2.73 (6H, s); 3.25 (2H, m); 3.87 (1H, m); 4.15 (2H, m); 7.52 (1H, d).

To a refluxing solution of 0.10 g of aminoguanidine hydrogencarbonate in 12 ml of 0.1M sodium hydroxide and 4 ml of ethanol a solution of 0.30 g of (E)-3-oxo-17β-guanidinoiminomethyl-5β-androstane-14β-ol acetate in 4 ml of ethanol was added dropwise. After 2 hrs at reflux temperature, the solution was evaporated to dryness under reduced pressure. The crude product was ground with water and the solid collected by filtration. After dissolution in ethanol, 0.10 g of oxalic acid were added to give 0.16 mg of the title compound (I-aw) as a white solid.

$^1$H-NMR (300 MHz, DMSO-d$_6$, ppm from TMS):
0.80 (3H, s); 0.90 (3H, s); 2.25 (1H, m); 2.70 (6H, s); 3.25 (2H, m); 3.87 (1H, m); 4.15 (2H, m); 7.50 (1H, d).

EXAMPLE 24

3-((EZ-Guanidinoimino)-17β-((E)-3-dimethylaminopropoxyiminomethyl)-5β-androstane-14β-ol (I-ax)

The title compound (I-ax) (0.17 g) was obtained as an oxalate salt, starting from 3-oxo-14β-hydroxy-5β-androstane-17β-carboxaldehyde (0.95 g) (Prepn. 6) and 2-dimethylaminoethoxyamine dihydrochloride using the same procedure described in Ex. 23.

$^1$H-NMR (300 MHz, DMSO-d$_6$, ppm from TMS):
0.80 (3H, s); 0.90 (3H, s); 2.25 (1H, m); 2.70 (6H, s); 3.15 (2H, m); 4.15 (2H, m); 7.50 (1H, d).

EXAMPLE 25

3-((EZ)-2-Imidazolin-2-ylhydrazono))-17β-((E)-2-dimethylaminoethoxyiminomethyl)-5β-androstane-14β-ol (I-ay)

The title compound (I-ay) (0.21 g) was obtained as a dioxalate salt, using the same procedure described in Ex. 23 starting from 3-oxo-14β-hydroxy-5β-androstane-17β-carboxaldehyde (0.90 g) (Prepn. 6) and using 2-dimethylaminopropoxyamine dihydrochloride, in the first step, and 2-hydrazino-2-imidazoline hydrobromide successively.

$^1$H-NMR (300 MHz, DMSO-d$_6$, ppm from TMS):
0.80 (3H, s); 0.90 (3H, s); 2.25 (1H, m); 2.60 (4H, s); 2.70 (6H, s); 3.25 (2H, m); 4.10 (2H, m); 7.50 (1H, d).

EXAMPLE 26

3-((EZ)-2-Dimethylaminoethoxyimino))-17β-((E)-2-dimethylaminoethoxyiminomethyl)-5β-androstane-14β-ol (I-az)

To a solution of 0.50 g of 2-dimethylaminoethoxyamine dihydrochloride, 2.50 g of sodium acetate in 35 ml of 0.2M acetic acid a solution of 0.40 g of 3-oxo-14β-hydroxy-5β-androstane-17β-carboxaldehyde (Prepn. 6) in 40 ml of dioxane was added dropwise. After 4 days at room temperature, the mixture was evaporated to dryness under reduced pressure. The crude product was purified by flash-chromatography (SiO$_2$) using chloroform/methanol 80/20; the fractions containing the title compound were collected and evaporated to dryness. After dissolution in ethyl acetate, 0.12 g of oxalic acid were added to give 0.18 mg of the title compound (I-az) as dioxalate, white solid.

$^1$H-NMR (300 MHz, DMSO-d$_6$, ppm from TMS):
0.75 (3H, s); 0.85 (3H, s); 2.25 (1H, m); 2.70 (12H, s); 3.25 (4H, m); 4.18 (4H, m); 7.55 (1H, d).

EXAMPLE 27

3-((EZ)-3-Dimethylaminopropoxyimino))-17β-((E)-3-dimethylaminopropoxyiminomethyl)-5β-androstane-14β-ol (I-ba)

The title compound (I-ba) (0.27 g) was obtained as dioxalate salt, starting from 3-oxo-14β-hydroxy-5β-androstane-17β-carboxaldehyde (0.90 g) (Prepn. 6) and 2-dimethylaminoethoxyamine dihydrochloride using the same procedure described in Ex. 26.

$^1$H-NMR (300 MHz, DMSO-d$_6$, ppm from TMS):
0.75 (3H, s): 0.85 (3H, s); 2.25 (1H, m); 2.65 (12H, s); 3.10 (4H, m); 4.10 (4H, m); 7.50 (1H, d).

PREPARATION 1

3β-Acetoxy-14β,17α-dihydroxy-5β-androstane-17β-carboxaldehyde (II-a)

A mixture of 1.60 g of 3β-acetoxy-14β-hydroxy-5β-androstane-17β-carboxaldehyde (Boutagy J. and Thomas R., Aust. J. Chem., 1971, 24, 2723), 0.83 g of selenium dioxide and 1.20 ml of pyridine in 20 ml of dioxane was heated at 80° C. for 12 hrs. After cooling the mixture was filtered and the filtrate washed with aqueous sodium hydrogencarbonate and extracted with ethyl acetate. The organic layer was dried over anhydrous sodium sulfate and evaporated to dryness. The crude product was purified by flash-chromatography (SiO$_2$) using n-hexane/ethyl acetate 6/4 as eluant; the fractions containing the title compound were collected and evaporated to give 0.55 g of the title compound (II-d) as a white solid.

$^1$H-NMR (300 MHz, CDCl$_3$, ppm from TMS): 0.80 (3H, s); 0.99 (3H, s); 2.08 (3H, s); 3.69 (1H, s); 5.11 (1H, m); 9.98 (1H, s).

PREPARATION 2

3β-(3-Aminopropoxy)-17β-(2-(1,3-dioxolanyl))-5β-androstan-14β-ol (II-b)

A solution of 6.00 g of 3β,14β-dihydroxy-5β-androstane-17β-carboxaldehyde (Boutagy J. and Thomas R., Aust. J. Chem., 1971, 24, 2723), 0.80 g of oxalic acid and 10.0 ml of ethylene glycol in 120 ml of acetonitrile was stirred at room temperature for 24 hrs. The mixture was made alkaline with aqueous sodium hydrogencarbonate and extracted with ethyl acetate; the organic layer was dried over anhydrous sodium sulfate and evaporated to dryness under reduced pressure to give 6.50 g of 17β-(2-(1,3-dioxolanyl))-5β-androstane-3β,14β-diol as a dense oil.

$^1$H-NMR (300 MHz, CDCl$_3$, ppm from TMS): 0.98 (3H,s); 1.05 (3H, s); 3.80–4.20 (5H, m); 4.98 (1H, d).

To a solution of 6.00 g of 17β-(2-(1,3-dioxolanyl))-5β-androstan-3β,14β-diol in 50 ml of dry tetrahydrofuran, 4.40 g of sodium hydride (60% dispersion in mineral oil) were added under nitrogen atmosphere at room temperature and the resulting mixture was stirred at reflux temperature for 6 hrs; 14.0 g of allyl bromide were added and the reflux continued for further 20 hrs. The mixture was quenched with water and the organic solvent was distilled under reduced pressure. The residue was extracted with ethyl acetate; the organic solution was dried over anhydrous sodium sulfate and evaporated to dryness under reduced pressure. The residue was purified by flash-chromatography (SiO$_2$) using n-hexane/ethyl acetate 80/20 as eluant to give 5.88 g of 3β-prop-(2-en)oxy- 17β(2-(1,3-dioxolanyl))-5β-androstan-14β-ol as a white solid.

¹H-NMR (300 MHz, CDCl$_3$, ppm from TMS): 0.97 (3H, s); 1.04 (3H, s); 2.74 (1H, dd); 3.69 (1H, bs); 3.80–4.20 (6H, m); 4.99 (1H, d); 5.12–5.18 (1H, m); 5.22–5.32 (1H, m); 5.87–6.01 (1H, m).

To a solution of 1.70 g of 9-borabicyclo[3.3.1]nonane in 350 ml of dry tetrahydrofuran, 5.00 g of 3β-prop-(2-en)oxy-17β-(2-(1,3-dioxolanyl))-5β-androstan-14β-ol in 100 ml of tetrahydrofuran were added under nitrogen atmosphere, at room temperature. The solution was stirred for 6 hrs then 7.5 ml of ethanol, 2.5 ml of 6N sodium hydroxide and 5 ml of hydrogen peroxide 30% were added. The mixture was stirred at 50° C. for one hr, quenched with a solution of 7.6 g of potassium carbonate in 200 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 4.05 g of 3β-(3-hydroxypropoxy)-17β-(2-(1,3-dioxolanyl))-5β-androstan-14β-ol as a white amorphous solid.

¹H-NMR (300 MHz, CDCl$_3$, ppm from TMS): 0.96 (3H, s); 1.05 (3H, s); 3.57–3.67 (3H, m); 3.80–4.20 (6H, m); 4.98 (1H, d).

A solution of 0.29 ml of diethyl azodicarboxylate was added dropwise, under nitrogen atmosphere, to a solution of 3.75 g of 3β-(2-hydroxypropoxy)-17β-(2-( 1,3-dioxolanyl))-5β-androstan-14β-ol, 1.24 g of phthalimide and 2.50 g of triphenylphosphine in 35 ml of tetrahydrofuran at room temperature. After 2 hrs the solvent was removed in vacuo, the crude product was dried over anhydrous sodium sulfate and evaporated to dryness under reduced pressure. The crude product was purified by flash-chromatography (SiO$_2$) using n-hexane/ethyl acetate 80/20 to give 3.50 g of 3β-(3-phthalimidopropoxy)-17β-(2-(1,3-dioxolanyl))-5β-androstan-14β-ol.

¹H-NMR (300 MHz, CDCl$_3$, ppm from TMS): 0.87 (3H, s); 1.03 (3H, s); 3.38–3.50 (2H, m); 3.52 (1H, m); 3.80–4.20 (6H, m); 4.99 (1H, d); 7.68–7.75 (2H, m); 7.80–7.90 (2H, m).

To a solution of 3.00 g of 3β-(3-phthalimidopropoxy)-17β-(2-(1,3-dioxolanyl))-5β-androstan-14β-ol in 300 ml of ethanol, 1.20 g of hydrazine hydrate were added at room temperature. The mixture was kept at reflux for 4 hrs, then 10 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 2.00 g of the title compound (II-b) as a white solid.

¹H-NMR: (300 MHz, CDCl$_3$, ppm from TMS): 0.95 (3H, s); 1.05 (3H, s); 2.60–2.80 (2H, m); 3.30–3.40 (2H, m); 3.58 (1H, bs); 3.80–4.20 (4H, m); 4.98 (1H, d).

PREPARATION 3

3β-(2-Aminoethoxy)-17β-(2-(1,3-dioxolanyl))-5β-androstan-14β-ol (II-c)

To a suspension of 5.5 g of NaH (60% dispersion in mineral oil) in 400 ml of dry tetrahydrofuran 7.0 g of 17β-(2-(1,3-dioxolanyl))-5β-androstan-3β,14β-diol (see Prepn. 2) were added at room temperature in a nitrogen atmosphere. The mixture was kept at reflux for 6 hrs, then 26 ml of bromoacetaldehyde diethylacetal were added and the suspension was stirred at reflux for 4 hrs. After cooling at room temperature 50 ml of water were added cautiously, and tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$) using n-hexane/ethyl acetate 80/20 as eluant to give 6.9 g of 3β-(2,2-diethoxyethoxy)-17β-(2-(1,3-dioxolanyl))-5β-androstan-14β-ol, as a dense oil.

1H NMR (300 MHz, CDCl$_3$, ppm from TMS): 0.97 (3H, s); 1.03 (3H, s); 1.24 (6H, t); 3.47–3.50 (2H, m); 3.50–3.80 (5H, m); 3.80–4.20 (4H, m); 4.62 (1H, t); 4.99 (1H, d).

A solution of 6.80 g of 3β-(2,2-diethoxyethoxy)-17β-(2-(1,3-dioxolanyl))-5β-androstan-14β-ol, in 550 ml of dioxane and 430 ml of a saturated aqueous solution of tartaric acid was heated at 70° C. for two hrs in a nitrogen atmosphere. After cooling at room temperature, 200 ml of water were added and the mixture was extracted with methylene chloride. The organic layer was washed with water, dried over anhydrous sodium sulfate and evaporated to dryness under reduced pressure. The crude product was purified by flash-chromatography (SiO$_2$) using as eluant n-hexane/ethyl acetate 70/30 to give 2.11 g of 3β-formylmethoxy-17β-(2-(1,3-dioxolanyl))-5β-androstan-14β-ol as a white waxy solid.

¹H NMR: (300 MHz, CDCl$_3$, ppm from TMS): 0.97 (3H, s); 1.03 (3H, s); 3.70 (1H, bs); 3.80–4.20 (4H, m); 4.10 (2H, d); 4.97 (1H, d); 9.75 (1H, t).

To a solution of 2.00 g of 3β-formylmethoxy-17β-(2-(1,3-dioxolanyl))-5β-androstan-14β-ol in 200 ml of methanol, 0.60 g of sodium borohydride were added slowly at 0° C. After 30 min. the temperature of the mixture was left to rise to 25° C. After 2 hrs 40 ml of water were added, methanol was distilled under reduced pressure, and the residue was extracted with methylene chloride; the organic layer was washed with water, dried over sodium sulfate and evaporated to dryness under reduced pressure. The crude product was purified by flash-chromatography (SiO$_2$) using n-hexane/ethyl acetate 80/20 as eluant to give 1.70 g of 3β-(2-hydroxyethoxy)-17β-(2-(1,3-dioxolanyl))-5β-androstan-14β-ol as a white solid.

¹H NMR (300 MHz, CDCl$_3$, ppm from TMS): 0.96 (3H, s); 1.04 (3H, s); 3.48 (2H, t); 3.63 (1H, bs); 3.70 (2H, t); 3.80–4.20 (4H, m); 4.98 (1H, d).

A solution of 0.60 ml of diethyl azodicarboxylate was added dropwise, under nitrogen, to a solution of 1.65 g of 3β-(2-hydroxyethoxy)-17β-(2-(1,3-dioxolanyl))-5β- androstan-14β-ol, 0.60 g of phthalimide and 1.00 g of triphenylphosphine in 15 ml of tetrahydrofuran was stirred at room temperature. After 2 hrs the solvent was removed in vacuo, the crude product was dried over anhydrous sodium sulfate and evaporated to dryness under reduced pressure. The crude product was purified by flash-chromatography (SiO2) using n-hexane/ethyl acetate 80/20 to give 1.65 g of 3β-(2-phthalimidoethoxy)-17β-(2-(1,3-dioxolanyl))-5β-androstan-14β-ol.

$^1$H NMR (300 MHz, CDCl$_3$, ppm from TMS): 0.95 (3H, s); 5 1.05 (3H, s); 3.60–3.68 (3H, m); 3.80–4.20 (6H, m); 4.98 (1H, d); 7.70–7.75 (2H, m); 7.80–7.90 (2H, m).

To a solution of 1.50 g of 31β-(2-phthalimidoethoxy)-17β-(2-(1,3-dioxolanyl))-5β-androstan-14β-ol in 90 ml of ethanol (96%) 0.50 ml of hydrazine hydrate were added at room temperature. The mixture was stirred at reflux for 4 hrs, then 20 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.75 g of the title compound (II-c) as a white solid.

$^1$H NMR: (300 MHz, CDCl$_3$, ppm from TMS): 0.97 (3H, s); 1.03 (3H, s); 2.84 (2H, t); 3.41 (2H, m); 3.65 (1H, bs); 3.80–4.20 (4H, m); 4.98 (1H, d).

PREPARATION 4

3β-(2-(1-Pyrrolidinyl)ethoxy)-17β-(2-(1,3-dioxolanyl))-5β-androstane-14β-ol (II-d)

A mixture of 3.20 g of 17β-(2-(1,3-dioxolanyl))-5β-androstane-3β,14β-diol (see Prepn. 2), 18.4 g of 1-(2-chloroethyl)pyrrolidine and 5.60 g of sodium hydride (55% dispersion in mineral oil) in 300 ml of dry tetrahydrofuran was refluxed for 12 hrs. After cooling, water was added and the mixture was extracted with ethyl acetate; the organic layer was dried over anhydrous sodium sulfate and evaporated to dryness under reduced pressure. The crude product was purified by flash-chromatography (SiO$_2$) using chloroform/methanol 95/5 as eluant; the fractions containing the title compound were collected and evaporated to give 2.55 g of the title compound (II-d) as a dense oil.

$^1$H-NMR (300 MHz, CDCl$_3$, ppm from TMS): 0.93 (3H, s); 1.04 (3H, s); 2.05 (1H, m); 2.85 (6H, m); 3.63 (3H, m); 3.80–4.13 (4H, m); 4.99 (1H, d).

PREPARATION 5

3β-(3-(1-Pyrrolidinyl)propoxy)-17β-(2-(1,3-dioxolanyl))-5β-androstane-14β-ol (II-e)

The title compound (II-e) (2.70 g) was obtained as a dense oil starting from 3.20 g of 17β-(2-(1,3-dioxolanyl))-5β-androstane-3β,14β-diol (see Prepn. 2) and 20.0 g of 1-(3-chloropropyl)pyrrolidine using the same procedure described in Prepn. 4.

$^1$H-NMR (300 MHz, CDCl$_3$, ppm from TMS): 0.93 (3H, s); 1.04 (3H, s); 2.05 (1H, m); 2.55 (6H, m); 3.42 (2H, t); 3.62 (1H, m); 3.80–4.13 (4H, m); 4.99 (1H, d).

PREPARATION 6

3-Oxo-14β-hydroxy-5β-androstane-17β-carboxaldehyde (II-f)

To a suspension of 0.88 g of pyridinium dicromate in 2.20 ml of dichloromethane a solution of 0.50 g of 3β,14β-dihydroxy-5β-androstane-17β-carboxaldehyde (Boutagy J. and Thomas R., Aust. J. Chem., 1971, 24, 2723) in 2.5 ml of dichloromethane was added at room temperature. After 20 hrs the mixture was diluted with diethyl ether and filtered through celite; the filtrate was evaporated to dryness under reduced pressure. The crude product was purified by flash-chromatography (SiO2) using n-hexane/ethyl acetate 6/4 eluant; the fractions containing the title compound were collected and evaporated to give 0.30 g of the title compound (II-f) as a white foam.

$^1$H-NMR (300 MHz, CDCl$_3$, ppm from TMS): 1.02 (3H, s); 1.06 (3H, s); 2.25–2.40 (1H, m); 2.62 (2H, m); 9.72 (1H, d).

What is claimed is:

1. A 17-Hydroxyiminomethyl-14β-hydroxy5β-androstane derivative compound of the formula I:

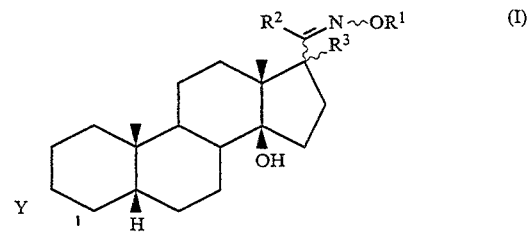

wherein:
the symbol ≡≡≡ represents a single or a double bond;
the symbol ∼∼ means α or β configuration or a Z or E configuration:
when --- is a single bond, Y represents β-OR$^4$;
when === is a double bond, Y represents a
N∼OR$^1$ or a N∼NHC(=N R$^5$)NR$^6$R$^7$ group;
R$^1$ represents C2–C6 alkyl substituted by one or more NR$^8$R$^9$ or NHC(=NH)NH$_2$;
R$^2$ represents hydrogen or methyl;
R$^3$ represents hydrogen or hydroxy;
R$^4$ represents hydrogen, C2–C4 alkyl unsubstituted or substituted by one or more NR$^{10}$R$^{11}$ or NHC(=NH)NH$_2$;
R$^5$ represents hydrogen, methyl or C2–C4 alkyl;
R$^6$, R$^7$ which may be the same or different, represent hydrogen, methyl or C2–C4 alkyl;
R$^8$, R$^9$ which may be the same or different, represent hydrogen, methyl or C2–C4 alkyl;
R$^{10}$, R$^{11}$ which may be the same or different, represent hydrogen, methyl or C2–C4 alkyl.

2. A composition comprising a stereoisomer, Z or E isomer, tautomer, optical isomer or pharmaceutically acceptable salt of a compound of the formula set forth in claim 1.

3. A compound as set forth in claim 1, which is selected from the group consisting of:
(E)-17β-(2-aminoethoxyimino)methyl-5β-androstane-3β,14βdiol,
(E)-17β-(3-aminopropoxyimino)methyl-5β-androstane-3β,14β-diol,
(E)-17β-(2-dimethylaminoethoxyimino)methyl-5β-androstane-3β,14β-diol,
(E)-17β-(3-dimethylaminopropoxyimino)methyl-5βandrostane-3β,14β-diol,
(E)-17β-(2-guanidinoethoxyimino)methyl-5β-androstane-3β,14β-diol,
(E)-17β-(3-guanidinopropoxyimino)methyl-5β-androstane-3β,14β-diol, (E)-20-(2-aminoethoxyimino)-5β-pregnane-3β,14β-diol, (E)-20-(2-dimethylaminoethyoxyimino)-5β-pregnane--3β,14β-diol, (E)-20-(3-aminopropoxyimino-5β-pregnane-3β,14β-diol, (E)-20-(3-dimethylaminopropoxyimino)-5β-pregnane-3β,14β-diol, (E)-17β-(2-aminoethoxyimino)methyl-5β-androstane-3β,14β,17α-triol, (E)-17β-(3-aminopropoxyimino)methyl-5β-androstane-3β,14β,17α-triol, (E)-17β-(2-dimethylaminoethoxyimino)methyl-5β-androstane-3β,14β,17α-triol, (E)-17β-(3-dimethylaminopropoxyimino)methyl-5β-androstane-3β,14β,17α-triol, (E)-17β-(2-guanidinoethoxyimino)methyl-5β-androstane-3β,14β,17α-triol, (E)-17β-(3-guanidinopropoxyimino)methyl-5β-androstane-3β,14β,17α-triol, (E)-20-(2-aminoethoxyimino)-5β-pregnane-3β,14β,17α-triol, (E)-20-(2-dimethylaminoethyoxyimino)-5β-pregnane-3β,14β,17α-triol, (E)-20-(3-aminopropoxyimino)-5β-pregnane-3β,14β,17α-triol, (E)-20-(3-dimethylaminopropoxyimino)-5β-pregnane-3β,14β,17α-triol, (E)-3β-(3-aminopropoxy)-17β-methoxyiminomethyl-5β-androstane-14β-ol, (E)-3β-(3-aminopropoxy-)17β-(2-aminoethoxyimino)methyl-5β-androstane-14β-ol, (E)-3β-(3-aminopropoxy-)17β-(3-aminopropoxyimino)methyl-5β-androstane-14β-ol, (E)-3β-(3-aminopropoxy-)17β-(2-dimethylaminopropoxyimino) methyl-5β-androstane-14β-ol, (E)-3β-(3-aminopropoxy-)17β-(3-dimethylaminoethoxyimino) methyl-5β-androstane-14β-ol, (E)-3β-(3-aminopropoxy)-17β-(2-guanidinopropoxyimino)-methyl-5β-androstane-14β-ol, (E)-3β-(3-aminopropoxy-)17β-(3-guanidinoethoxyimino)-methyl-5β-androstane-14β-ol, (E)-3β-(3-aminopropoxy)-20-(2-aminopropoxyimino)-5β-pregnane-14β-ol, (E)-3β-(3-aminopropoxy)-20-(2-dimethylaminoethoxyimino)-5β-pregnane-14β-ol, (E)-3β-(3-aminopropoxy)-20-(3-aminopropoxyimino)-5β-pregnane-14β-ol, (E)-3β-(3-aminopropoxy)-20-(3-dimethylaminopropoxyimino)-5β-pregnane-14β-ol, (E)-3β-(3-aminopropoxy)-17β-methoxyiminomethyl-5β-androstane-14β,17α-diol, (E)-3β-(3-aminopropoxy)-17β-(2-aminoethoxyimino)methyl-5β-androstane-14β,17α-diol, (E)-3β-(3-aminopropoxy)-17β-(3-aminopropoxyimino)methyl-5β-androstane-14β,17α-diol, (E)-3β-(3-aminopropoxy)-17β-(2-dimethylaminoethoxyimino)-methyl-5β-androstane-14β,17α-diol, (E)-3β-(3-aminopropoxy)-17β-(3-dimethylaminopropoxy-imino)methyl-5β-androstane-14β-17α-diol, (E)-3β-(3-aminopropoxy)-17β-(2-guanidinoethoxyimino)-methyl-5β-androstane-14β,17α-diol, (E)-3β-(3-aminopropoxy)-17β- (3-guanidinopropoxyimino)methyl-5β-androstane-14β-17α-diol, 3-((EZ)-guanidinoimino)-17β-((E)-2-aminoethoxyiminomethyl)-5β-androstane-14β-01, 3-((EZ)-guanidinoimino)-17β-((E)-3-aminopropoxyiminomethyl)-5β-androstane-14β-01, 3-((EZ)-guanidinoimino)-17β-((E)-2-dimethylaminoethoxyiminomethyl)-5β-androstane-14β-01, 3-((EZ)-guanidinoimino)-17β-((E)-3-dimethylaminopropoxyiminomethyl)-5β-androstane-14β-01, 3-((EZ)-2-dimethylaminoethoxyimino)-17β-((E)-2-dimethylaminoethoxyiminomethyl)-5β-androstane-14β-01, 3-((EZ)-3-dimethylaminopropoxyimino)-17β-((E)-3-dimethylaminopropoxyiminomethyl)-5β-androstane-14β-01, the corresponding (Z) isomers of the aforementioned (E) isomers, and the corresponding 3β-(3-dimethylaminopropoxy), 3β-(3-diethylaminopropoxy), 3β-(2-aminoethoxy), 3β-(2-dimethylaminoethoxy), and 3β-2-diethylaminoethoxy) analogs of said 3β-(3-aminopropoxy) compounds.

4. A pharmaceutical composition comprising a compound of general formula I as set forth in claim 1 and a pharmaceutically acceptable carrier and/or diluent.

5. The compound according to claim 1, which is (E)-17β-(2-dimethylaminoethoxyimino)methyl-5β-androstane-3β, 14β-diol.

* * * * *